(12) United States Patent
Ozawa et al.

(10) Patent No.: US 8,062,592 B2
(45) Date of Patent: Nov. 22, 2011

(54) ELECTROPHORESIS APPARATUS USING CAPILLARY ARRAY AND A SAMPLE TRAY

(75) Inventors: Miho Ozawa, Abiko (JP); Ryoji Inaba, Hitachinaka (JP); Tomohiro Shoji, Hitachinaka (JP); Manabu Akiba, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 464 days.

(21) Appl. No.: 12/175,998

(22) Filed: Jul. 18, 2008

(65) Prior Publication Data

US 2009/0020429 A1    Jan. 22, 2009

(30) Foreign Application Priority Data

Jul. 18, 2007   (JP) ................................. 2007-187233

(51) Int. Cl.
*G01N 35/10*    (2006.01)

(52) U.S. Cl. ........................................ 422/63; 204/604

(58) Field of Classification Search ............... 422/62–67; 204/604

See application file for complete search history.

(56) References Cited

U.S. PATENT DOCUMENTS

| 5,529,679 | A | 6/1996 | Takahashi et al. |
| 6,660,233 | B1 | 12/2003 | Coassin et al. |
| 2001/0040096 | A1 | 11/2001 | Yamamoto et al. |
| 2002/0023839 | A1* | 2/2002 | Inaba et al. .................. 204/451 |
| 2006/0006066 | A1 | 1/2006 | Yamazaki et al. |
| 2007/0184548 | A1* | 8/2007 | Tan et al. .................. 435/303.1 |

FOREIGN PATENT DOCUMENTS

| JP | 2776208 | 7/1998 |
| JP | 11-502937 | 3/1999 |
| JP | 2001-324474 | 11/2001 |
| JP | 2006-29814 | 2/2006 |
| WO | WO 97/26539 | 7/1997 |

OTHER PUBLICATIONS

Mayer, B. X., et al., "Long-Term Analysis with Capillary Electrophoresis", LC-GC Europe, Jan. 2001, p. 2-7.*
http://www.beckmancoulter.com/products/instrument/geneticanalysis/ceq/ceq8800_inst_dcr.asp, retrieved Jul. 7, 2008.

* cited by examiner

*Primary Examiner* — Jeffrey T Barton
*Assistant Examiner* — J. Christopher Ball
(74) *Attorney, Agent, or Firm* — McDermott Will & Emery LLP

(57) ABSTRACT

Even if a standby time to the measurement becomes long, a sample in a sample container is prevented from deteriorating. A cooling mechanism is provided in a sample tray for holding a sample plate, or in a plate-mounting portion of a table-type auto sampler of a capillary electrophoresis apparatus, so that the sample plate is cooled during the measurement also.

3 Claims, 10 Drawing Sheets

A-A' cross section

ELECTROPHORESIS APPARATUS USING CAPILLARY ARRAY AND A SAMPLE TRAY

BACKGROUND OF THE INVENTION

1. Field of the Invention

The present invention relates to capillary electrophoresis apparatuses. Particularly, the present invention relates to a capillary electrophoresis apparatus that separates and analyzes samples, such as DNA or proteins, using a plurality of capillaries, and to a sample tray used in the separation analysis by this electrophoresis apparatus.

2. Description of the Related Art

In recent years, a capillary electrophoresis apparatus has been used widely in which a capillary is filled with an electrophoresis medium (separation medium), such as a polymer gel or a polymer solution.

A capillary electrophoresis apparatus, as described in, for example, Patent Document 1 (Japanese Patent No. 2776208), has a high heat dissipation capacity enabling application of a high voltage to a sample as compared with a conventionally used flat-plate electrophoresis apparatus. Accordingly, the capillary electrophoresis apparatus has the advantage of performing electrophoresis at high speed. Moreover, the capillary electrophoresis apparatus has a lot of advantages, such as that a far less amount of sample is required, and that the automated filling of a separation medium and the automated injection of samples are possible, and therefore, it has been utilized in various separation-analysis measurements, such as DNA and protein analyses.

This DNA sequencer includes a mechanism, using a syringe or a pump, capable of automatically filling the capillary with a polymer (separation medium) and automatically injecting the capillary with a sample, and so on. With this mechanism, the separation-analysis measurement of samples can be carried out continuously even without man power, for example in all-night operation.

Incidentally, a sample to be subjected to electrophoresis analysis is usually dispensed in a container while being dissolved in a solvent. For example, when the separation analysis of DNA is to be carried out, the DNA to be analyzed is amplified in advance using an approach, such as PCR (polymerase chain reaction). For this reason, a sample plate for thermal cycler and a sample tube for PCR which have been used in the amplification reaction of DNA by the PCR apparatus are often used subsequently as the sample container also at the time of the separation-analysis measurement of this purified DNA using the capillary electrophoresis apparatus.

Accordingly, when the sample purified by the amplification reaction with the PCR apparatus is measured using the capillary electrophoresis apparatus, there is no need to take the trouble to transfer the sample to another container for this measurement. Thus, the separation-analysis measurement can be conveniently performed using the capillary electrophoresis apparatus on the sample without transferring the sample. Moreover, the attaching of such a sample plate to an adapter as shown in Patent Document 2 (Japanese Patent Publication (Kokai) No. 2001-324474 A) facilitates automated transport of samples inside the apparatus.

Patent Document 1: Japanese Patent No. 2776208
Patent Document 2: Japanese Patent Publication (Kokai) No. 2001-324474 A
Patent Document 3: Japanese Patent Publication (Kokai) No. 2006-29814 A
Patent Document 4: JP Patent Publication (Kohyo) No. 11-502937 A (1999)
Non-Patent Document 1: "Various kinds of plates and electrophoresis buffers", Beckman Coulter, Inc., URL: http://www.beckmancoulter.co.jp/product/product01/CEQ_plate.html, [online] searched on June 16, Heisei 20 (2008)

SUMMARY OF THE INVENTION

The present inventor has found the following problems after the devoted study.

When separation-analysis measurement is continuously performed on samples using a capillary electrophoresis apparatus, as many samples to be measured as the number of times of measurement need to be set in the apparatus in advance. For this reason, as the number of times of measurement increases, the number of samples set in the apparatus also increases.

As an example of a generally used sample plate (sample container), there is a sample plate (384-well plate) that is capable of mounting 384 samples thereon, the sample plate having 384 (16×24=384) wells (sample holes) in which samples are introduced and held. With such a sample plate, a maximum of 48 times of continuous measurements will be carried out for samples on two of the sample plates, using the capillary electrophoresis apparatus that can perform separation-analysis measurement simultaneously on 16 samples in one measurement.

Accordingly, in such a case, if the separation-analysis measurement to be carried out takes one hour for one measurement, it will take 47 hours after the separation-analysis measurement of the first sample is started until the separation-analysis measurement of the last sample is started. Thus, for a sample to be measured later, the standby time after the sample is set in the apparatus until its own measurement is started will be considerably long.

On the other hand, among samples, such as DNA samples labeled with fluorescence, for example, on which separation-analysis measurement is performed by an electrophoresis apparatus, some samples have difficulties in accurate measurement because of the degeneration or deterioration of the samples, such as the decomposition of a fluorescent substance when the samples are left at normal temperature for a long time.

In order to solve this problem, it is necessary to prevent the deterioration of samples that are set in the apparatus during the standby time after the sample is set in the apparatus until its own separation-analysis measurement is started. Specifically, for the purpose of achieving an accurate separation-analysis measurement, it is preferable that the samples set inside an electrophoresis apparatus be cold-stored at an appropriate temperature so that the samples may not deteriorate during the standby time after the samples are set inside the apparatus until the own measurements are started.

For example, Patent Document 3 (Japanese Patent Publication (Kokai) No. 2006-29814 A) describes an electrophoresis apparatus including a sample plate storage bath capable of storing while cooling a large number of sample plates that are waiting for measurement.

Described is that sample plates waiting for measurement among a plurality of sample plates set inside the apparatus are cooled and stored in this sample plate storage bath. As a result, during the standby time until the measurement is started by the electrophoresis analysis unit, the samples held in wells of the sample plates can be cooled, and the deterioration of the samples can be suppressed. Then, in carrying out the measurement, the sample plate is taken out from this sample plate storage bath and is conveyed to the electrophoresis analysis unit, where the separation-analysis measurement is carried out for the sample held in the wells.

For this reason, in the case of the separation-analysis measurement requiring a high measurement throughput and a large number of sample plates to be set, a capillary electrophoresis apparatus provided with the sample plate storage bath having such a cooling function, when used, can efficiently cool and store the sample plates waiting for the measurement to be started.

However, in a capillary electrophoresis apparatus having a low measurement throughput and a small number of sample plates to be set, such a number of sample plates that are cold-stored using the sample plate storage bath with the cooling function will not be used.

In such a capillary electrophoresis apparatus having a low measurement throughput and a small number of sample plates to be set, a table type auto sampler is frequently used, in which sample plates as well as necessary reagents and the like are arranged on a table.

In the capillary electrophoresis apparatus provided with this table type auto sampler, the sample plates are directly set at a predetermined position on the table of the auto sampler in advance for the measurement. Then, the table itself is suitably moved so that a sample subjected to separation-analysis measurement can be introduced into a capillary from the well where the sample is held.

In such a capillary electrophoresis apparatus having a low measurement throughput and a small number of sample plates to be set, it is important to suppress the deterioration of a sample held at each well of the sample plate during the standby time after the sample plate is directly set at a predetermined position on the table of the auto sampler in advance until the separation-analysis measurement of a sample to be measured in the last is started. While the deterioration of the sample is suppressed, the measurement should be performed in a way that the temperature condition of the sample held at each well may not be changed from the state of the initial measurement condition, and thereby the temperature condition at the time of separation-analysis measurement for each sample held at each well may not vary from one sample to another.

Moreover, another capillary electrophoresis apparatus provided with a denaturing function is disclosed in Non-Patent Document 1. This function is for heating a microtiter plate but not for preventing the degeneration or deterioration of a sample held at a sample plate.

Against the above-described background, an object of the present invention is to prevent a sample held at a sample plate from degenerating or deteriorating when the sample plate is placed on an auto sampler.

In the present invention, a cooling mechanism is provided in a sample tray for holding a sample plate or in an auto sampler of a capillary electrophoresis apparatus so as to cool the sample plate.

Since the degeneration or deterioration of a sample on the auto sampler can be suppressed according to the present invention, the reliability of the electrophoresis data is improved.

DESCRIPTION OF THE PREFERRED EMBODIMENTS

Hereinafter, capillary electrophoresis apparatuses according to embodiments of the present invention and a sample tray used therefor will be described with reference to the accompanying drawings.

Figure 1:
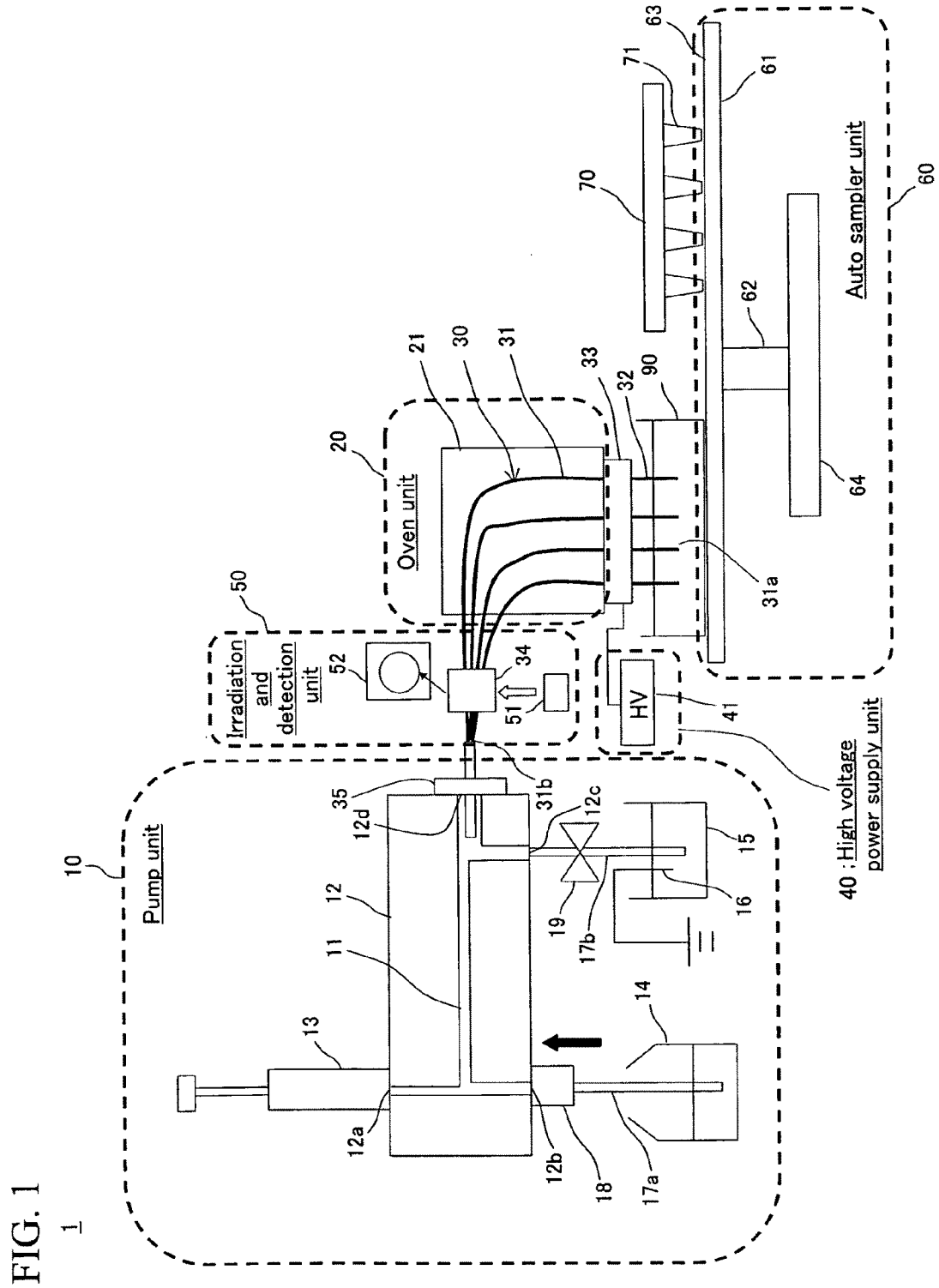
FIG. 1 is a schematic block diagram of a capillary electrophoresis apparatus as one embodiment of the present invention.

FIG. 1 is a schematic block diagram of a capillary electrophoresis apparatus as one embodiment of the present invention. In FIG. 1, a capillary electrophoresis apparatus 1 of this embodiment includes a pump unit 10, an oven unit 20, a capillary array 30, a high voltage power supply unit 40, an irradiation and detection unit 50, and an auto sampler unit 60.

The pump unit 10 is for filling each capillary 31 of the capillary array 30 with a separation medium (resolving gel). The pump unit 10 includes a polymer block 12 having: a flow path 11 formed therein; and four flow path connectors 12a to 12d in the surface thereof, the flow path connectors 12a to 12d communicating with this flow path 11. The flow path 11 inside the polymer block 12 communicates, through these flow path connectors 12a to 12c, with a syringe 13, a polymer bottle 14, and a buffer jar 15 that similarly constitute the pump unit 10. A capillary head 35 of the capillary array 30 is connected to the flow path connector 12d, so that the flow path 11 communicates with each capillary 31, as well.

In the pump unit 10 having such a configuration, the syringe 13 constitutes a liquid-sending means for a separation medium in filling the capillary 31 with the separation medium. Moreover, the polymer bottle 14 is a container that stores therein the separation medium so that the capillary 31 can be supplied with the separation medium. Moreover, the buffer jar 15 is a container for storing therein a buffer solution in which an electrolyte is dissolved. In the buffer jar 15, there is provided a grounding electrode 16 for keeping this stored buffer solution at the earth potential.

A polymer tube 17a communicates between the flow path 11 inside the polymer block 12 and the polymer bottle 14. The polymer tube 17a is provided with a check valve 18 that prevents the separation medium, which is sucked from the polymer bottle 14 to the flow path 11 side, from flowing backwards to the polymer bottle 14 side. Similarly, a buffer side tube 17b communicates between the flow path 11 inside the polymer block 12 and the buffer jar 15. The buffer side tube 17b is provided with a valve 19 for carrying out the opening and closing of the buffer side tube 17b.

In the pump unit 10 having such a configuration, while the buffer side tube 17b is closed by the valve 19, the separation medium is sucked from the polymer bottle 14 into the syringe 13 and the flow path 11 in accordance with the operation and movement of a plunger (not illustrated) provided in the syringe 13. Then, the separation medium sucked into this syringe 13 and the flow path 11 is delivered to each capillary 31 of the capillary array 30 through the flow path connector 12d of the polymer block 12.

The oven unit 20 includes an oven 21 with a temperature adjusting element such as a Peltier element. Inside the oven 21, the plurality of capillaries 31 constituting the capillary array 30 are housed. The oven 21 operates and controls the temperature adjusting element to maintain the temperature inside the chamber to a predetermined temperature suitable for the analysis of a target sample by electrophoresis. The oven unit 20 reduces a difference in the electrophoresis speeds of samples caused by each temperature difference of the plurality of capillaries 31 of the capillary array 30.

The capillary array 30 is formed of, for example, a fused quartz tube having an inner diameter of 50±10 μm and an outer diameter of 340±20 μm, the external surface of which is coated with a polyimide film having a thickness of 15±5 μm. The plurality of (e.g., 16) capillaries 31 as hollow members in which a sample is subjected to electrophoresis separation, are integrally held in the capillary array 30.

One end of each capillary 31 is a sample injection side 31a for injecting a sample into the capillary 31 from a later-described well 71 of a sample plate 73. For this reason, the one end of each capillary 31 is inserted into a conductive pipe 32 formed of a conductive member (e.g., stainless steel), and secured to the conductive pipe 32 while the sample injection side 31a is exposed a little from the conductive pipe 32.

Moreover, the one end of each capillary 31 and the conductive pipe 32, through which each capillary 31 is inserted, are integrally held by a load header 33, while having a predetermined arrangement relation of one row or a two-dimensional arrangement. The electrical connection with the apparatus is guaranteed by means of the conductive pipe 32 of the one end of each capillary 31 and an electrode provided in the load header 33 for supporting the capillary 31 and the conductive pipe 32.

On the other hand, in the middle of each capillary 31, the polyimide coating on the outer surface is removed, this removed portion corresponding to a length and a position of each capillary 31, to thereby form a light irradiated portion that is to be irradiated with excitation light. The light irradiated portions of the capillaries 31 are aligned in a row in parallel to each other by means of a detection window 34, and is integrally arranged and fixed. The detection window 34 can apply excitation light to the light irradiated portion of each capillary 31, and detect, from the light irradiated portion, fluorescence that is generated from a fluorescent-labeled sample by the irradiation of this excitation light, the fluorescent-labeled sample being injected into each capillary 31.

The other end of each capillary 31 is a polymer injection side 31b. The capillaries 31 are bundled into one by the capillary head 35, and are integrally and securely held. The capillary head 35 is liquid-tightly but detachably connected to the above-described flow path connector 12d of the pump unit 10, and the resultant capillary head 35 has a pressure resistance.

Then, the capillary array 30 having the plurality of capillaries 31 aligned and integrally held can be also freely housed in/taken out from the oven 21, and the capillary array 30 itself is exchangeable in the capillary electrophoresis apparatus 1.

The capillary portion, of such a capillary array 30, between the load header 33 and the detection window 34 is housed in the oven 21 so that the temperature of this portion may be kept uniform and constant.

In this embodiment, the sample injection side 31a of the capillary array 30 is positioned at a predetermined position inside the apparatus in relation to the later-described movable configuration of a table 61 of the auto sampler unit 60.

The high voltage power supply unit 40 includes a high voltage power supply 41 for generating a high voltage of around 15 kV, for example. The high voltage power supply 41 is wire-connected to, for example, the electrode provided in the load header 33 of the capillary array 30, and supplies a high voltage generated by the high voltage power supply 41. Thereby, in the state where each conductive pipe 32 of the capillary array 30 is immersed in a sample inside the well 71 of the sample plate 73 that is arranged on the auto sampler unit 60 or in the state where each conductive pipe 32 is immersed in a buffer solution of a buffer reservoir 90, a high voltage of the high voltage power supply unit 40 can be applied from each conductive pipe 32, serving as the sample injection side electrode, to the sample or the buffer solution via the electrode provided in the load header 33.

The irradiation and detection unit 50 includes: an irradiation optical system 51 for delivering excitation light to the detection window 34; and a detection optical system 52 for detecting fluorescence from the detection window 34.

The irradiation optical system 51, using a mirror, a beam splitter, a condenser lens, and the like, delivers the excitation light generated by an excitation light source, such as a laser or an LED, to the light irradiated portions of the capillaries 31, which are integrally arranged and fixed to the detection window 34.

On the other hand, the detection optical system 52 includes a detection lens, a CCD camera, and a computer. The detection optical system 52: disperses the fluorescence, which is emitted from the detection window 34 by irradiation of the excitation light and transmitted through the detection lens, for each wavelength; produces an image on the CCD camera; and detects this image as an image signal. Then, this image signal is processed by the computer for the analysis of the sample.

The auto sampler unit 60 moves the sample tray 70 and each container, such as the buffer reservoir 90, for holding reagents required for the electrophoresis measurement, to the load header 33 of the capillary array 30, i.e., to the sample injection side 31a of the aligned plurality of capillaries 31.

Figure 2:
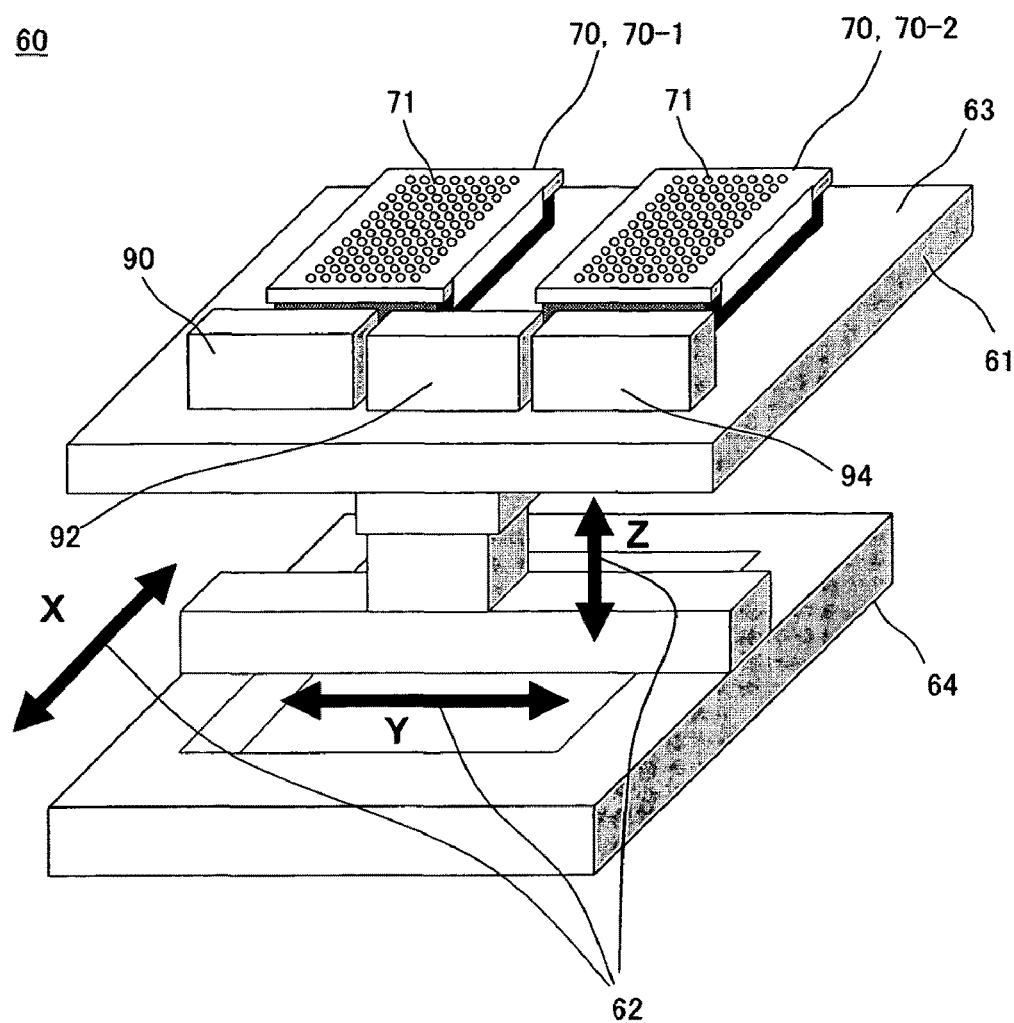
FIG. 2 is a perspective view of an auto sampler unit used in the capillary electrophoresis apparatus of this embodiment.

FIG. 2 is a perspective view of this auto sampler unit for describing the schematic configuration of the auto sampler unit.

In the illustrated example, the auto sampler unit 60 includes a table 61 and a table transfer mechanism 62.

In this case, the table 61 is formed of a board-like member having a rectangular, planar table top 63. The table transfer mechanism 62, as shown in FIG. 2, moves the table 61 formed of this board-like member, to an auto sampler base 64 using a non-illustrated actuator in three orthogonal axis directions of a back-and-forth direction (X axis direction), a right-and-left direction (Y axis direction), and vertical top-and-down direction (Z axis direction), thereby moving and adjusting the position of the table top 63 to an arbitrary three-dimensional position.

On the front side, of the drawing, in the X direction of the table top 63, a buffer reservoir holder capable of detachably holding the buffer reservoir 90, a washing water reservoir holder capable of detachably holding a washing water reservoir 92, and a waste reservoir holder capable of detachably holding a waste reservoir 94 are formed in this order along the Y direction in the drawing.

On the other hand, at the rear portion, of the drawing, in the X direction of the table top 63, a sample tray holder capable of detachably holding a plurality (two in the illustrated example) of sample trays 70-1, 70-2 is formed along the Y direction in the drawing.

Here, the buffer reservoir 90 is a container for storing the buffer solution in which the sample injection side 31a of each of the plurality of capillaries 31 of the capillary array 30 is immersed during the electrophoresis. The sample injection side 31a of the capillary array 30 and the top end of the conductive pipe 32, which have been immersed in a sample liquid (sample solution) or the buffer solution, are immersed in a washing solution (water) in order to prevent the contamination of the separation medium inside the capillary 31. The washing water reservoir 92 is a container for holding this washing solution (water) that washes the above-described sample injection side 31a of the capillary array 30 and the top end of the conductive pipe 32. The waste reservoir 94 is a container that holds water for dissolving the waste separation medium and stores the used separation medium which is discharged from each capillary 31 of the capillary array 30 at the time of exchanging separation media.

Next, the configuration of the sample tray 70 of this embodiment is described with reference to FIG. 2 and FIG. 3.

Figure 3:
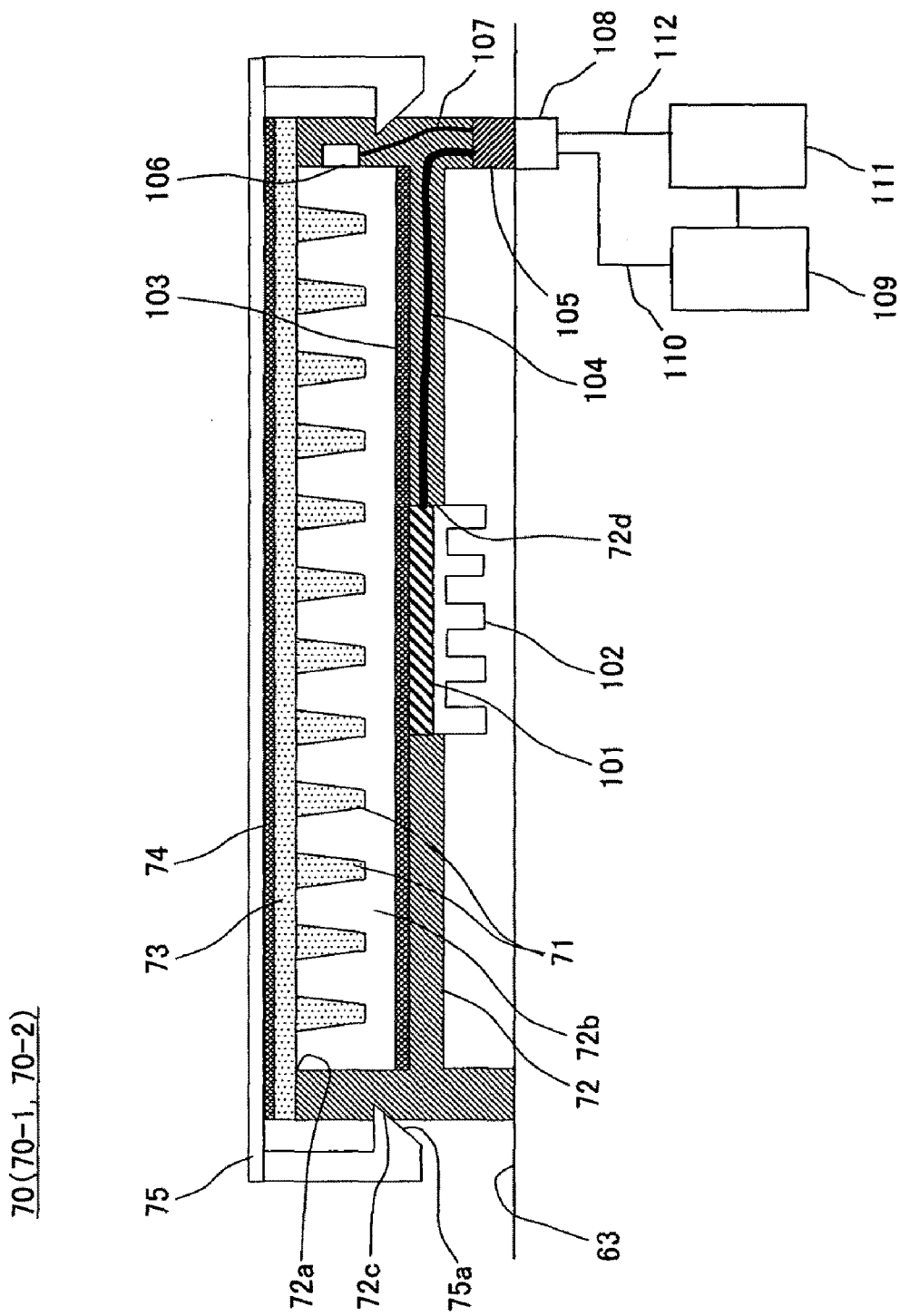
FIG. 3 is a cross sectional view of a sample tray of this embodiment, and is a block diagram of a cooling mechanism of a capillary electrophoresis apparatus according to a first embodiment.

FIG. 3 is a cross sectional view of the sample tray of this embodiment.

The sample tray 70 (70-1, 70-2) is a sample holding member for holding a plurality of samples to be measured by electrophoresis. The sample tray 70 includes a sample tray base 72 as an adapter, a sample plate 73 for holding a plurality of samples, a septa 74 that prevents the sample from evaporating, and a clip 75 that engages with the sample tray base 72 to integrally hold the sample plate 73 and the septa 74 to the sample tray base 72.

The sample plate 73, which is covered with the septa 74 in order to prevent the evaporation of the sample, is fixed to the sample tray base 72 with the clip 75, and is integrally positioned and mounted, together with the sample tray base 72, to the sample tray holder of the table top 63 of the auto sampler unit 60.

In the illustrated example, the sample tray base 72 is formed of a closed-end box with legs, the top surface of which is opened as a receiving opening 72a of the sample plate 73. The interior of the box is a well receiving space 72b that is opened to the outside through the receiving opening 72a. Moreover, an engagement groove 72c that engages with a locking portion 75a of the clip 75 is formed at a predetermined position of the peripheral surface of the sample tray base 72 so that the clip 75 may be detachably attached.

In the sample plate 73, wells 71 as sample holding container portions for injecting and holding a sample solution are formed in an array. The top surface of the well 71 is opened. In the illustrated example, in the sample plate 73, the 384 wells 71 as a total are formed in an array of 16 rows×24 columns. Thereby, 384 samples can be placed on the single sample plate 73. The upper surface side of the sample plate 73 is a flat surface where each well 71 is opened, while on the lower surface side the container portion of each well 71 projects. The circumferential portion of the sample plate 73 is sandwiched by the opening end of the sample tray base 72 and the clip 75.

The septa 74 is a rubber sheet that is arranged so as to cover the upper surface side of the sample plate 73 in order to prevent evaporation of the sample solution. In the septa 74, a notch (not illustrated) for inserting therein the conductive pipe 32 on the sample injection side of the capillary 31 is formed at a position corresponding to each well 71. This notch will spread by a pressing force of the sample injection side when the sample injection side of the capillary 31 is inserted through the notch, so that the sample injection side 31a of the capillary 31 and the conductive pipe 32 can be inserted into the well 71. Except when the sample injection side of the capillary 31 is being inserted, the notch of the septa 74 is closed so as to prevent evaporation of the sample solution inside the well 71. Furthermore, the notch lip of this notch can also wipe out the sample and the like having adhered to the sample injection side of the capillary 31 when the conductive pipe 32 and the sample injection side 31a of the inserted capillary 31 exit from the interior of the well 71.

Note that, in place of the septa 74, a film may be stuck to the upper surface of the sample plate 73 for the purpose of preventing evaporation of the sample, and prior to injecting the sample a through-hole may be formed at a position through which the sample injection side 31a of the capillary 31 is inserted.

The clip 75 includes a plate-like portion having through-holes (not illustrated) formed therein at positions corresponding to the respective wells 71 of the sample plate 73. The sample injection side 31a of the capillary 31 can be inserted through the through-hole. The clip 75 is shaped to have a leg portion at a tip end thereof, the leg portion extending from a side of the plate-like portion. The leg portion has the locking portion 75a that can engage with the engagement groove 72c of the sample tray base 72.

Then, after the septa 74 is arranged to cover the sample tray base 72, on which the sample plate 73 is mounted, the locking portion 75a of the clip 75 is locked with the engagement groove 72c of the sample tray base 72, thereby configuring the sample tray 70.

Figure 4:
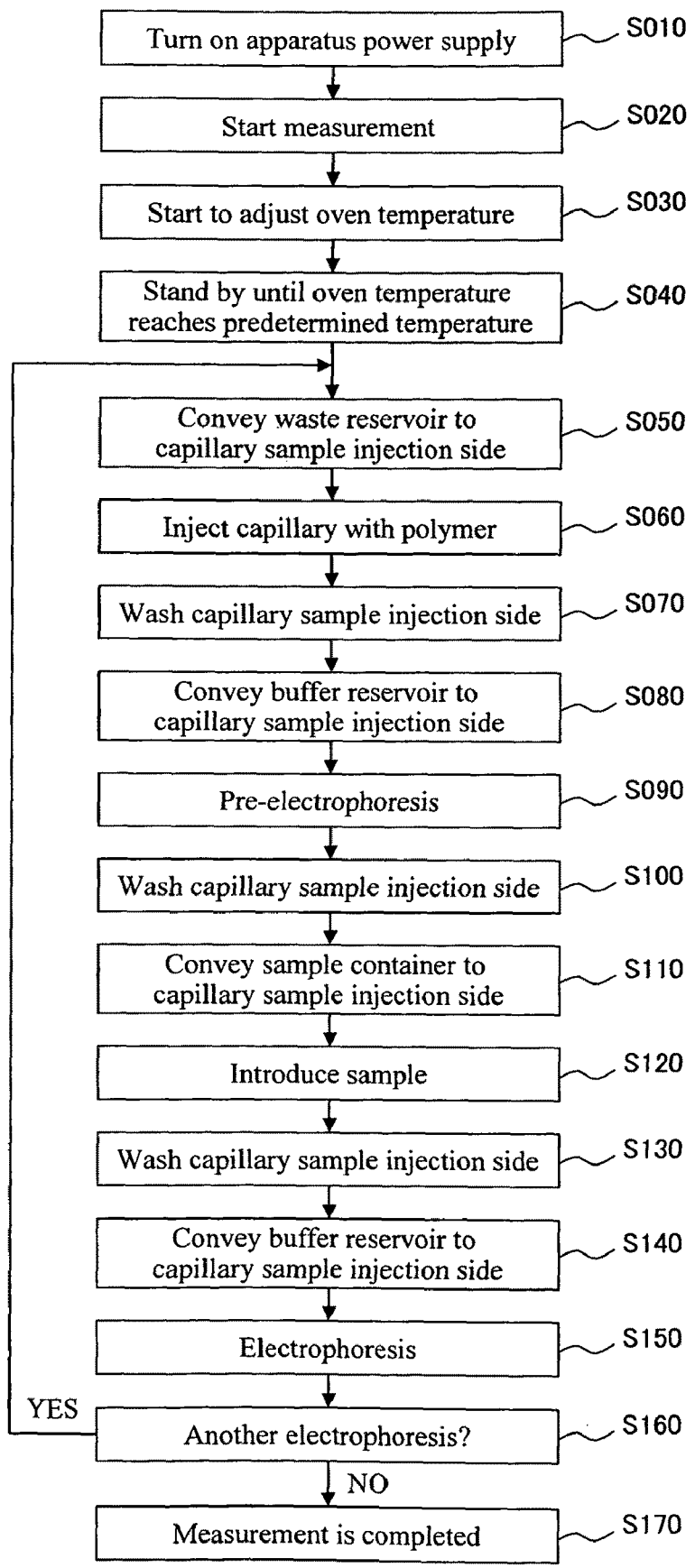
FIG. 4 is a flowchart showing a flow of measurements of the capillary electrophoresis of this embodiment.

In the capillary electrophoresis apparatus 1 with the above-described configuration, the measurement is carried out as shown in FIG. 4.

FIG. 4 is a flowchart showing a flow of the measurement of the capillary electrophoresis. The capillary electrophoresis apparatus 1 is activated by turning on the apparatus power supply (S010). When the measurement processing with respect to the sample tray 70, which is held in advance in the sample tray holder on the table 61 of the auto sampler unit 60, is started (S020), firstly, the temperature adjustment is started so that the temperature of the oven 21 of the oven unit 20 for housing therein the capillary array 30 may be set to a predetermined temperature suitable for the pre-designed analysis of a target sample by the electrophoresis (S030).

In this case, the capillary electrophoresis apparatus 1 will standby without carrying out the next processing until the temperature of the oven 21 reaches the predetermined temperature (S040). In this standby state during this temperature adjustment, the auto sampler unit 60 moves the table 61 to locate the buffer reservoir 90 on the table 61 to an array position underneath the load header 33 of the capillary array 30, and immerses the sample injection side of the capillary 31 into the buffer solution. This is for preventing drying of the separation medium of the sample injection side 31a that is in the standby state, and for preventing degeneration due to the drying of the separation medium inside the capillary 31, the drying causing degradation of the measurement accuracy, such as degradation of the resolution during the electrophoresis.

Then, when the temperature of the oven 21 reaches the predetermined temperature, the auto sampler unit 60 moves the table 61 so as to move the buffer reservoir 90 from the sample injection side 31a of the capillary 31. Thereafter, in order to discharge the waste separation medium inside the capillary 31, the waste reservoir 94 on the table 61 is moved to the array position to immerse the sample injection side of the capillary 31 into the water of the waste reservoir 94 (S050). Then, the capillary electrophoresis apparatus 1 closes the valve 19, and injects the capillary 31 with the separation medium, which is sucked from the polymer bottle 14 by operating and moving the plunger of the syringe 13. Thus, the existing separation medium inside the capillary 31 is pushed out to the waste reservoir 94, and thereby the separation medium inside the capillary 31 is replaced (S060).

Upon completion of the injection of the separation medium, the auto sampler unit 60 moves the table 61 so as to move the waste reservoir 94 from the sample injection side 31a of the capillary 31. Thereafter, in order to wash this sample injection side, the auto sampler unit 60 moves the washing water reservoir 92 on the table 61 to the array position, and then immerses the sample injection side into the washing water, which is stored in the washing water reservoir 92, to thereby remove the waste separation medium having adhered to the outer surfaces of the capillary sample injection side 31a and conductive pipe 32 (S070).

Upon completion of the washing of the sample injection side 31a of the capillary 31 and the conductive pipe 32, the auto sampler unit 60 moves the table 61 so as to move the washing water reservoir 92 from the sample injection side 31a of the capillary 31, and thereafter moves the buffer reservoir 90 to the array position to thereby immerse the sample injection side of the capillary 31 into the buffer solution (S080).

The capillary electrophoresis apparatus 1, while the sample injection side of the capillary 31 is immersed into the buffer solution, opens the valve 19, and applies a high voltage generated by the high voltage power supply 41 to between the conductive pipe 32 and the grounding electrode 16 to carry out pre-electrophoresis (S090). In this pre-electrophoresis, in a state where there is no sample in the separation medium inside the capillary 31, a current is caused to flow through an current-carrying path formed by the separation medium inside the capillary 31, thereby stabilizing the characteristic of the separation medium during the electrophoresis as describe later.

When the capillary electrophoresis apparatus 1 stops the high voltage application to complete the pre-electrophoresis, the auto sampler unit 60 moves the table 61 so as to move the buffer reservoir 90 from the sample injection side 31a of the capillary 31, and thereafter moves the washing water reservoir 92 to the array position to thereby immerse the sample injection side of the capillary 31. Thus, the buffer solution having adhered to the outer surfaces of the sample injection side 31a and conductive pipe 32 is removed (S100).

Upon completion of the washing of the sample injection side 31a of the capillary 31 and the conductive pipe 32, the auto sampler unit 60 moves the table 61 so as to move the washing water reservoir 92 from the sample injection side 31a of the capillary 31, and thereafter moves the sample tray 70, in which the sample plate 73 is integrally held, to the array position to thereby immerse the sample injection side of the capillary 31 into the sample solution inside the well 71 of the sample plate 73. In the well 71, the electrophoresis in this time is to be carried out (S110). Thereby, between the conductive pipe 32 and the grounding electrode 16, the current-carrying path is formed by the sample inside the well 71 and the separation medium inside the capillary 31.

The capillary electrophoresis apparatus 1, while the sample injection side 31a of the capillary 31 and the conductive pipe 32 are immersed in the sample solution to be measured, applies a high voltage generated by the high voltage power supply 41 to the conductive pipe 32 to thereby electrodynamically introduce the sample into the separation medium inside the capillary 31 (S120).

When the capillary electrophoresis apparatus 1 stops the high voltage application to complete the injection of the sample into the separation medium inside the capillary 31, the auto sampler unit 60 moves the table 61 so as to move the well 71 of the sample plate 73 from the sample injection side 31a of the capillary 31, and thereafter moves the washing water reservoir 92 to the array position to thereby immerse the sample injection side of the capillary 31 into the washing water. Thus, the sample solution having adhered to the outer surfaces of the sample injection side 31a and conductive pipe 32 is removed (S130).

Upon completion of the washing of the sample injection side 31a of the capillary 31 and the conductive pipe 32, the auto sampler unit 60 moves the table 61 so as to move the washing water reservoir 92 from the sample injection side 31a of the capillary 31, and thereafter moves the buffer reservoir 90 to the array position to thereby immerse the sample injection side of the capillary 31, in which the sample has been already injected, into the buffer solution (S140).

After the sample injection side 31a of the capillary 31 and the conductive pipe 32 are immersed into the buffer solution, the capillary electrophoresis apparatus 1 applies, as an electrophoresis voltage, a high voltage generated by the high voltage power supply 41 to the conductive pipe 32 to carry out the electrophoresis of the introduced sample (S150).

In the electrophoresis, when the introduced sample migrates inside the capillary 31 filled with the separation medium and passes therethrough, depending on the size of the sample, a sample having the lowest resistance of sample transmission moves the fastest. Thus, the smaller the size of the sample introduced into the sample injection side 31a, the faster the time when the sample reaches the detection window 34. At this moment, the detection optical system 52 detects the fluorescence generated from the sample introduced into the capillary 31, the fluorescence generated by the excitation light that is emitted from the irradiation optical system 51 to the light irradiated portion of the capillary 31. Then, on the basis of this detected fluorescence, analysis on the sample currently held in the corresponding well 71 of the sample plate 73 is conducted.

Upon completion of the electrophoresis in this manner, the capillary electrophoresis apparatus 1 determines whether or not the electrophoresis has been completed with respect to all the samples held in the respective wells 71 of the sample plate 73 of the sample tray 70, and also determines whether or not there is another electrophoresis (S160). When there is another electrophoresis, the auto sampler unit 60 moves the table 61 so as to move the buffer reservoir 90 from the sample injection side 31a of the capillary 31, and thereafter moves the waste reservoir 94 to the array position (S050). After the capillary 31 is filled with a fresh separation medium (S060), the next sample is subjected to the electrophoresis analysis by similarly carrying out the processings of Step S070 and the subsequent steps. On the other hand, if there is no other electrophoresis, the measurement based on the electrophoresis is completed (S170).

In order to prevent deterioration of the sample, the sample plate 73 will be cold-stored until it is mounted on the auto sampler unit 60 of the apparatus. However, once the sample plate 73 is mounted in the apparatus, a sample on the sample plate 73 to be measured later will be exposed to normal temperature for a long time during the standby time until its own measurement since the separation analysis based on the electrophoresis shown in Steps S50 to S150 described above is repeated. As a result, the sample is caused to be deteriorated.

For this reason, the capillary electrophoresis apparatus 1 and the sample tray 70 of this embodiment include a cooling mechanism in order to suppress the deterioration of a sample inside the well 71 of the sample plate 73 due to the standby time for measurement.

Hereinafter, a cooling means for the sample plate 73 during the standby time for measurement is described for each embodiment.

Embodiment 1

A cooling mechanism of a capillary electrophoresis apparatus according to a first embodiment is described with reference to FIG. 2 and FIG. 3.

A mounting hole 72d is formed in the center of a bottom portion of the sample tray base 72. In the mounting hole 72d, a Peltier element 101 is provided with the endothermic surface (cooling surface) thereof facing the well receiving space 72b side and the exothermic surface (heat-radiating surface) thereof facing the outside of the sample tray 70, that is, opposite to the well receiving space 72b side. Moreover, in the mounting hole 72d, there is provided a heat sink 102 abutting on the exothermic surface of the Peltier element 101. A concavo-convex shaped heat-radiating portion of the Peltier element 101 is exposed to the outside of the sample tray base 72. The heat sink 102 substantially increases the area of the exothermic surface (radiating surface) of the Peltier element 101.

Moreover, approximately the whole region of the bottom surface of the well receiving space 72b of the sample tray base 72 is covered with a metal plate 103 as a cooling plate. The metal plate 103 also abuts on the endothermic surface of the Peltier element 101 to substantially increase the area of the endothermic surface (cooling surface) of the Peltier element 101. In this embodiment, an aluminium thin plate is used taking into consideration the cooling effect of the well receiving space 72b and the convenience in conveying the sample tray 70.

Due to these heat sink 102 and metal plate 103, the heat absorption (cooling) of the well receiving space 72b by the Peltier element 101 can be carried out efficiently.

Note that, as required, a heat conductive sheet, such as a silicon sheet or a resin sheet, having electrical insulation and thermal conductivity is stuck to the surface, facing the sample plate 73, of the metal plate 103, and then insulation processing is performed thereon. This, in the case of the capillary electrophoresis, is for the purpose of preventing an electric discharge between the capillary 31 and the metal plate 103 in relation to the following steps of: inserting the sample injection side 31a of the capillary 31 into the well 71 of the sample plate 73; applying a high voltage to the both ends of the capillary 31; and electro-dynamically introducing the sample into the capillary 31.

Additionally, one end of a power cable 104 is connected to the Peltier element 101, and the other end thereof is connected to a connector 105 arranged in one of leg portions of the sample tray base 72. Furthermore, in this embodiment, in an inner wall of the sample tray base 72, a sensor 106 for detecting the temperature of the well receiving space 72b is provided so as to face the well receiving space 72b. A communication cable 107 routed from the sensor 106 is also connected to the connector 105.

On the other hand, a connector 108 is provided in the sample tray holder on the table top 63 of the auto sampler unit 60 on which the sample tray 70 is to be mounted. The connector 108 can be connected to the connector 105, and corresponds to a positioning mounting-position of the leg portion of the sample tray base 72, in which the connector 105 is arranged. The connector 108 is connected to a power cable 110 led out from a driver circuit 109 of the Peltier element 101, and also connected to a communication cable 112 of a thermal control circuit 111 that controls the temperature of the well receiving space 72b by drive-controlling the driver circuit 109. Thus, in this embodiment, when the sample tray 70 is mounted in the sample tray holder of the auto sampler unit 60, the power cables 104 and 110 as well as the communication cables 107 and 112 are electrically conducted to each other between the connectors 105 and 108.

When such conduction is made, a temperature detection signal of the well receiving space 72b of the sample tray base 72, which the sample plate 73 having been separately cold-stored by that time faces, will be supplied from the sensor 106 to the thermal control circuit 111. The thermal control circuit 111 drive-controls the driver circuit 109 on the basis of the supplied temperature detection signal, and operation-controls the Peltier element 101 so that the temperature of the sample plate 73, i.e., the well receiving space 72b of the sample tray base 72, which the sample plate 73 faces, may be kept at a predetermined cooling temperature.

In this embodiment, when the Peltier element 101 provides cooling by means of the endothermic surface (cooling surface), the cold air is transmitted all over the bottom surface of the well receiving space 72b through the metal plate 103, and is transmitted to the atmosphere (air) in the well receiving space 72b. For this reason, the wells 71 formed in an array on the sample plate 73 are also cooled almost uniformly without receiving an influence of the array position on the sample plate 73 relative to the Peltier element 101, and the sample dispensed in each well 71 is also cooled.

Accordingly, each sample inside the well 71 on the sample plate 73 of the sample tray 70 will be held at a predetermined cooling temperature by the cooling mechanism having the above-described configuration after the sample tray 70 is mounted on the auto sampler unit 60 for the electrophoresis measurement until the electrophoresis measurement of all the samples is completed and the sample tray 70 is conveyed from the auto sampler unit 60.

As a result, with regard to the sample plate 73 that is set in the capillary electrophoresis apparatus 1 for electrophoresis measurement, the deterioration of a sample, held in the well, to be measured later, can be suppressed.

Moreover, the temperature condition at the time of measurement of a sample held at each well 71 of the sample plate 73 will not change among the samples after the measurement starts. Accordingly, even if the standby time for measurement is extremely long, the degeneration or deterioration of samples can be prevented, and the samples can be used until the last electrophoresis measurement without being degraded, and therefore the reliability of the electrophoresis data is improved.

Note that, in this embodiment, the sensor 106 and the thermal control circuit 111 are provided in the sample tray 70, and the thermal control circuit 111 drive-controls the driver circuit 109 on the basis of the output of the sensor 106. However, instead of providing the sensor 106 and the thermal control circuit 111, the Peltier element 101 may be constantly driven only by the driver circuit 109.

Moreover, although in this embodiment the circuit portion of the driver circuit 109 is arranged on the auto sampler unit 60 side, it may be arranged on the sample tray 70 side.

Embodiment 2

A cooling mechanism of a capillary electrophoresis apparatus according to a second embodiment is described with reference to FIG. 5. Note that, hereinafter, in describing the embodiments, the components which are the same as or similar to those of the capillary electrophoresis apparatus 1 and the sample tray 70 according to the above-described embodiment are given the same reference numerals in the drawing, and the description thereof is omitted.

Figure 5:
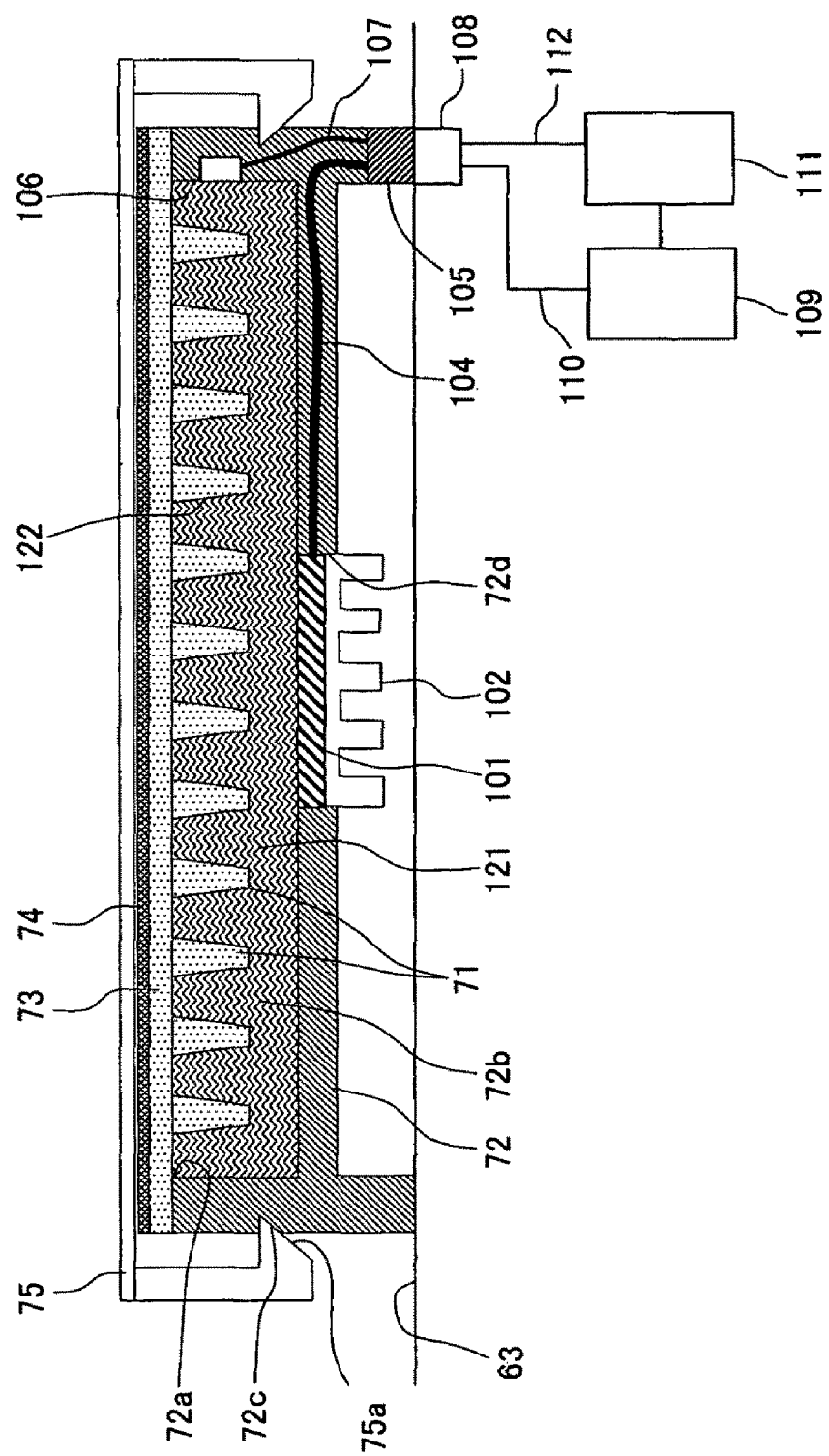
FIG. 5 is a block diagram of a cooling mechanism of a capillary electrophoresis apparatus according to a second embodiment.

FIG. 5 is a block diagram of the cooling mechanism of the capillary electrophoresis apparatus according to this embodiment.

In the first embodiment, the transmission of cold air between the metal plate 103 and the sample plate 73 is carried out using the atmosphere in the well receiving space 72b as the medium. Meanwhile, in this embodiment, the above-described transmission is carried out using a cooling block 121 made of a metal having an excellent thermal conductivity as the medium, thereby improving the efficiency of cooling the sample plate 73 by the Peltier element 101.

In this embodiment, in place of the above-described aluminum plate constituting the metal plate 103, the cooling block 121 made of aluminium in a shape that conforms to the shape of the well receiving space 72b is used, and this cooling block 121 is arranged in the well receiving space 72b of the sample tray base 72.

Accordingly, the outer shape of the cooling block 121 is shaped conforming to the inner surface shape of the sample tray base 72, which forms the well receiving space 72b. The cooling block 121 abuts on the inner peripheral wall portion in addition to the bottom portion of the well receiving space 72b of the sample tray base 72. Moreover, in a facing surface of the cooling block 121 where the cooling block 121 faces the sample plate 73, that is on the opening side of the well receiving space 72b, there is formed a well receiving hole 122 that fits onto and corresponding to the well 71 formed on the sample plate 73. In this embodiment, since the cooling block 121 is arranged in the sample tray base 72 which serves as an adapter to the electrophoresis apparatus for the sample plate 70, the cold-storage of samples is possible while maintaining ease of the automated conveyance of samples.

In this embodiment, the cooling block 121 and the sample tray base 72 are configured separately. However, the cooling block 121 and the sample tray base 72 may be integrally formed of the same member, and the outer surface thereof may be suitably covered with a heat-insulating member.

Embodiment 3

Figure 6:
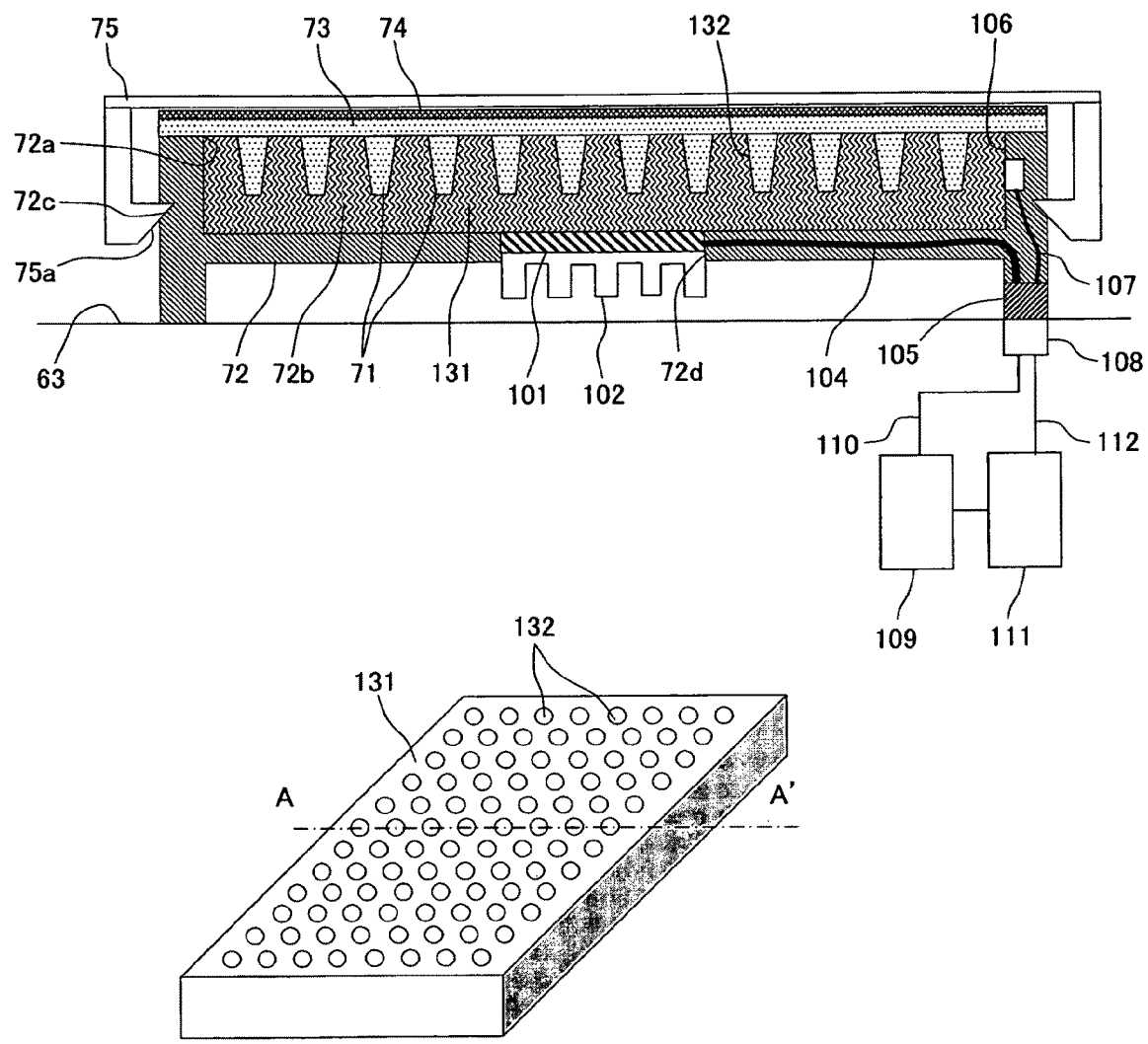
FIG. 6 is a block diagram of a cooling mechanism of a capillary electrophoresis apparatus according to a third embodiment.
Figure 6:

A cooling mechanism of a capillary electrophoresis apparatus according to a third embodiment is described with reference to FIG. 6. FIG. 6 is the block diagram of the cooling mechanism of the capillary electrophoresis apparatus according to this embodiment.

In this embodiment, in place of the cooling block 121 described in the second embodiment, formed is a sealed container 131, the outer shape of which conforms to the shape of the well receiving space 72b. The sealed container 131 includes the well receiving hole 132, and is filled with a coolant 132. The resultant sealed container 131 is arranged in the well receiving space 72b of the sample tray base 72.

According to this embodiment, the cooling efficiency can be improved and also a reduction in weight of the sample tray 73 can be achieved.

Note that, also in this embodiment, the metal plate 103 as the cooling plate may be provided on the bottom surface of the well receiving space 72b of the sample tray base 72.

Embodiment 4

Figure 7:
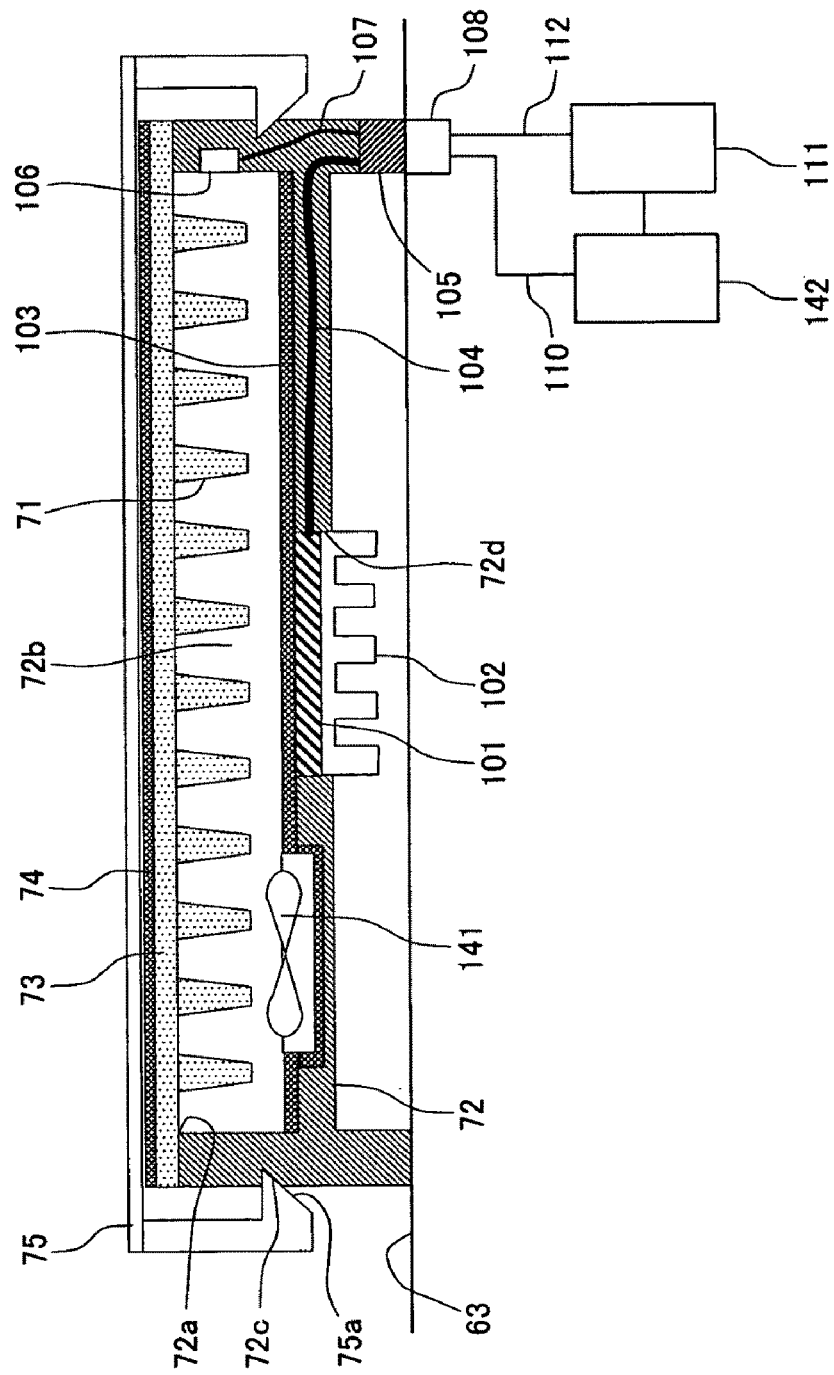
FIG. 7 is a block diagram of a cooling mechanism of a capillary electrophoresis apparatus according to a fourth embodiment.

A cooling mechanism of a capillary electrophoresis apparatus according to a fourth embodiment is described with reference to FIG. 7. FIG. 7 is a block diagram of the cooling mechanism of the capillary electrophoresis apparatus according to this embodiment.

In this embodiment, a stirring fan 141 is provided in the bottom surface or side surface of the well receiving space 72b of the sample tray base 72 in the sample tray 73 having the same configuration as that in the first embodiment, and the cold air generated by the Peltier element 101 and transmitted to the metal plate 103 is diffused within the well receiving space 72b by rotating the fan 141.

Note that, in the drawing, reference numeral 142 represents a driver circuit for the Peltier element 101 and the fan 141. The power cables 104 and 110 represent a power cable assembly that puts together the power cables respectively for the Peltier element 101 and the fan 141.

In this embodiment, the wells 71 formed in an array on the sample plate 73 are cooled more uniformly without receiving an influence of the array position on the sample plate 73 relative to the Peltier element 101, and the sample dispensed in each well 71 is also cooled uniformly.

Embodiment 5

Figure 8:
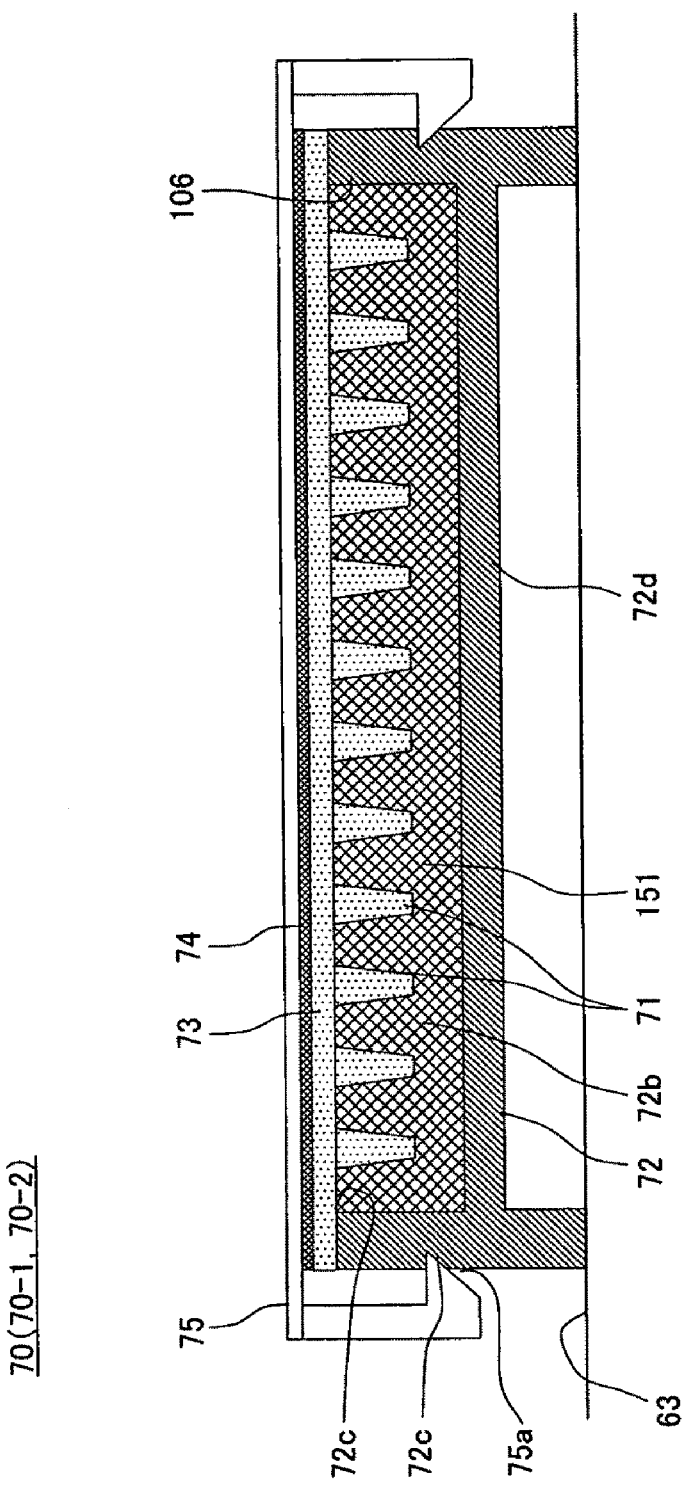
FIG. 8 is a block diagram of a cooling mechanism of a capillary electrophoresis apparatus according to a fifth embodiment.

A cooling mechanism of a capillary electrophoresis apparatus according to a fifth embodiment is described with reference to FIG. 8. FIG. 8 is a block diagram of the cooling mechanism of the capillary electrophoresis apparatus according to this embodiment.

In this embodiment, instead of providing the Peltier element 101 as the cooling mechanism, the well receiving space 72b of the sample tray base 72 is filled with an ice or coolant 151. In this case, for example, the sample tray base 72 itself is formed of a highly heat-insulating member, or the external surface of the sample tray base 72 is covered with a heat-insulating sheet, so that the thermal insulation property of the sample tray base 72 may be improved. As a result, the sample plate 73 can be cooled for many hours.

Embodiment 6

Figure 9A:
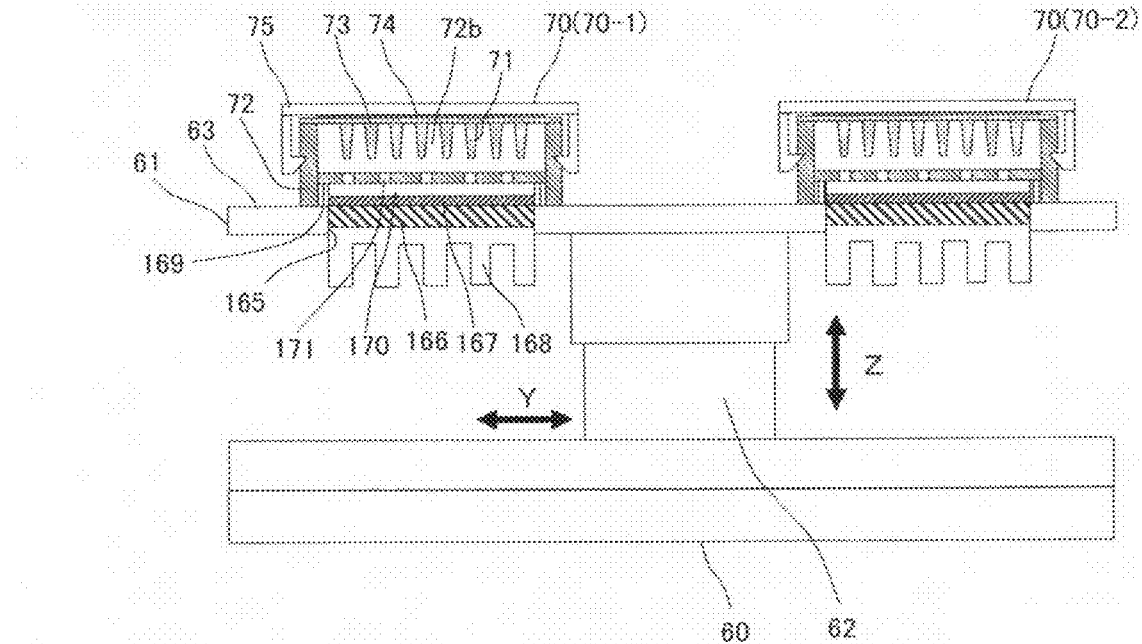
FIG. 9A and FIG. 9B are block diagrams of a cooling mechanism of a capillary electrophoresis apparatus according to a sixth embodiment.
Figure 9B:
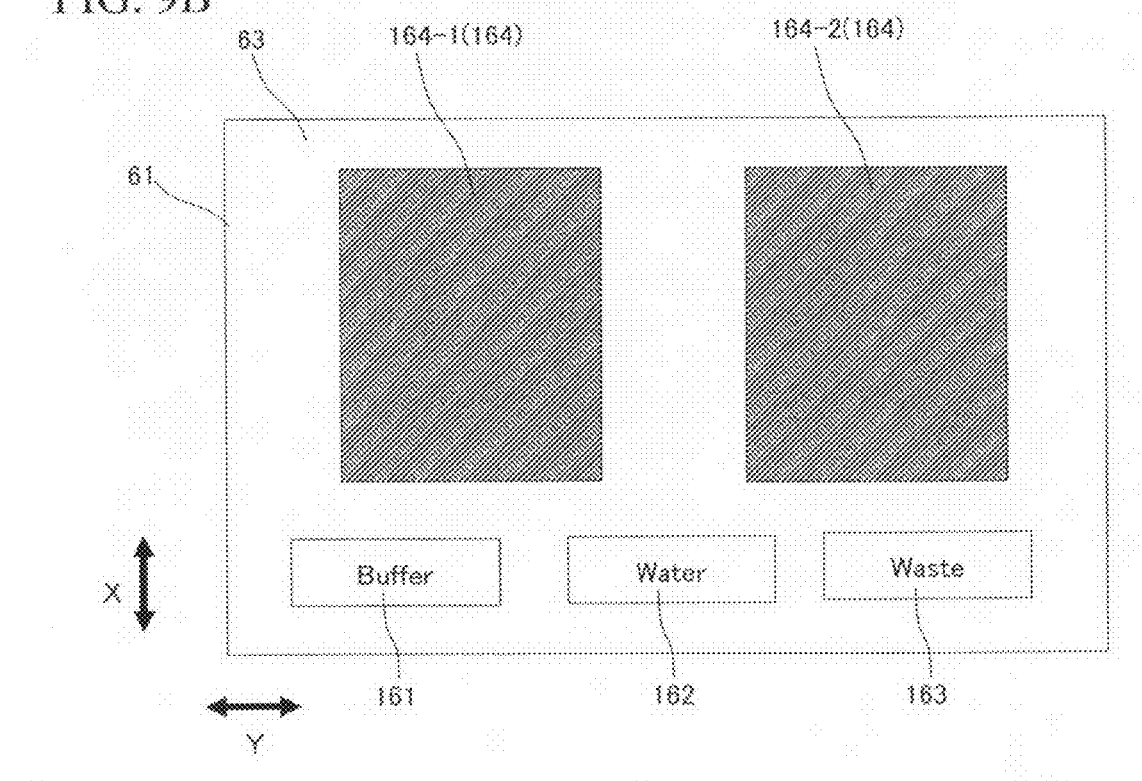

A cooling mechanism of a capillary electrophoresis apparatus according to a sixth embodiment is described with reference to FIG. 9A and FIG. 9B. FIG. 9A and FIG. 9B are block diagrams of the cooling mechanism of the capillary electrophoresis apparatus according to this embodiment.

FIG. 9A is a front schematic block diagram of the auto sampler unit 60 in this embodiment, and FIG. 9B is a plane block diagram of the table. Note that, hereinafter, in describing the embodiment, the components which are the same as or similar to those in the configuration of the above-described auto sampler unit 60 shown in FIG. 2 are given the same reference numerals in the drawing, and the description thereof is omitted.

This embodiment is characterized in that the cooling mechanism of the capillary electrophoresis apparatus 1 is arranged in the table 61 of the auto sampler unit 60 but not in the sample tray 70 unlike the first to fifth embodiments.

On the front side, of FIG. 9B, in the X direction of the table top 63, a buffer reservoir holder 161 capable of detachably holding the buffer reservoir 90, a washing water reservoir holder 162 capable of detachably holding the washing water reservoir 92, and a waste reservoir holder 163 capable of detachably holding the waste reservoir 94 are formed in this order along the Y direction in the drawing.

On the other hand, at the back, of the drawing, in the X direction of the table top 63, sample tray holders 164 (164-1, 164-2) capable of detachably holding a plurality of (two in the illustrated example) sample trays 70 (70-1, 70-2) are formed in this order along the Y direction in the drawing.

A mounting hole 165 is formed in a table portion corresponding to the sample tray holder 164 of the table 61.

In the mounting hole 165, a Peltier element 166 is provided, with the endothermic surface (cooling surface) thereof facing the table top 63, i.e., the mounting side of the sample tray 70, and the exothermic surface (heat-radiating surface) thereof facing the rear surface side, that is, opposite to the table top 63. The endothermic surface of the Peltier element 166 is arranged so as to project toward the same plane as that of the table top 63 or toward the table top 63, and the direction in which heat is absorbed by the Peltier element 166 is restricted to the direction of the bottom side of the sample tray 70, so that the bottom of the sample tray 70 can be cooled efficiently. Furthermore, a metal plate 167 as the cooling plate is provided abutting on the endothermic surface of the Peltier element 166, so that the whole area of the sample tray holder 164 can be cooled efficiently. The metal plate 167 is formed of a thin plate made of aluminium, for example. Moreover, in the mounting hole 165, a heat sink 168 is provided abutting on the exothermic surface of the Peltier element 166, so that a concavo-convex shaped heat-radiating portion thereof is exposed to the rear surface side of the table 61.

On the other hand, the sample tray 70 is formed so that the leg portions of the sample tray base 72 may surround the sample tray holder 164 and the metal plate 167. A positioning portion 169 corresponding to the sample tray holder 164 of the sample tray base 72 is formed in the inner peripheral surface of the leg portion. In the illustrated example, the positioning portion 169 abuts on the outer periphery surface of the metal plate 167. The bottom of the sample tray base 72 is faced to the Peltier element 166 and the metal plate 167. Thus, the sample tray base 72 is held so as not to slide on the table top 63.

Then, a space 170 sealed with respect to the outside is formed in the sample tray 70 by using the leg portions and the bottom portion of the sample tray base 72 and the metal plate 167. The space 170 communicates with the well receiving space 72b of the sample tray base 72, which the sample plate 73 faces, via a communicating hole 171 formed in the bottom of the sample tray base 72.

In this embodiment, when the Peltier element 166 is driven by a non-illustrated driver circuit and the Peltier element 166 carries out cooling by means of this endothermic surface (cooling surface), this cold air is transmitted to the space 170, which the bottom of the sample tray base 72 faces, via the metal plate 167. Furthermore, the cold air is conducted through the communicating hole 171 formed in the bottom of the sample tray base 72, as well as through the bottom itself, and is further transmitted to the atmosphere (air) in the well receiving space 72b.

For this reason, also in the case of this embodiment, as in the embodiments described above, the sample in each well 71 on the sample plate 73 of the sample tray 70 is held at a predetermined cooling temperature by the cooling mechanism having the above-described configuration after the sample tray 70 is mounted on the auto sampler unit 60 for the electrophoresis measurement until the electrophoresis measurement of all the samples is completed and the sample tray 70 is conveyed from the auto sampler unit 60. Accordingly, the deterioration of the sample, held in the well 71, to be measured later can be suppressed.

Moreover, the temperature condition at the time of measurement of a sample held at each well 71 of the sample plate 73, a change will not change among the samples after the measurement starts. Accordingly, even if the standby time for measurement is extremely long, the degeneration or deterioration of samples can be prevented, and the samples can be used until the last electrophoresis measurement without being degraded, and therefore the reliability of the electrophoresis data is improved. Furthermore, in the case of this embodiment, since the cooling mechanism is arranged on the table 61 side of the auto sampler unit 60, the cooling mechanism can be shared among a plurality of sample trays 70.

Note that, in this embodiment, with the use of the bottom of the sample tray base 72, a new space is formed, in which the well receiving space 72b and the space 170 are always communicating with each other through the communicating hole 171. However, this bottom may be removed, and with the use of the sample plate 73, the leg portions of the sample tray base 72, and the metal plate 167, a single closed space sealed with respect to the outside may be formed in the sample tray 70 on the table top 63.

Embodiment 7

Figure 10A:
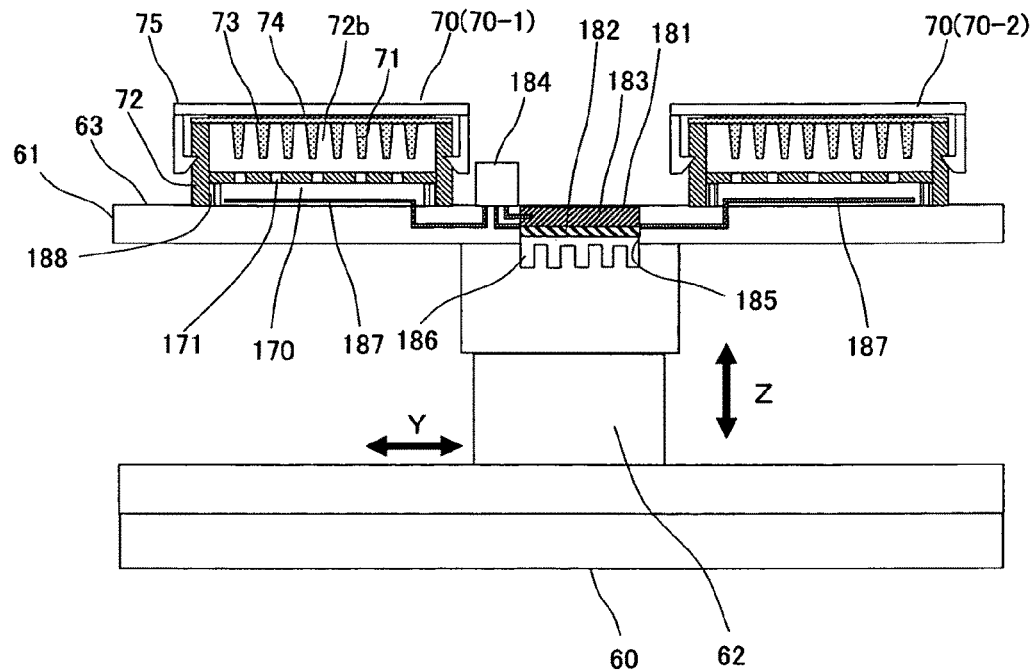
FIG. 10A and FIG. 10B are block diagrams of a cooling mechanism of a capillary electrophoresis apparatus according to a seventh embodiment.
Figure 10B:
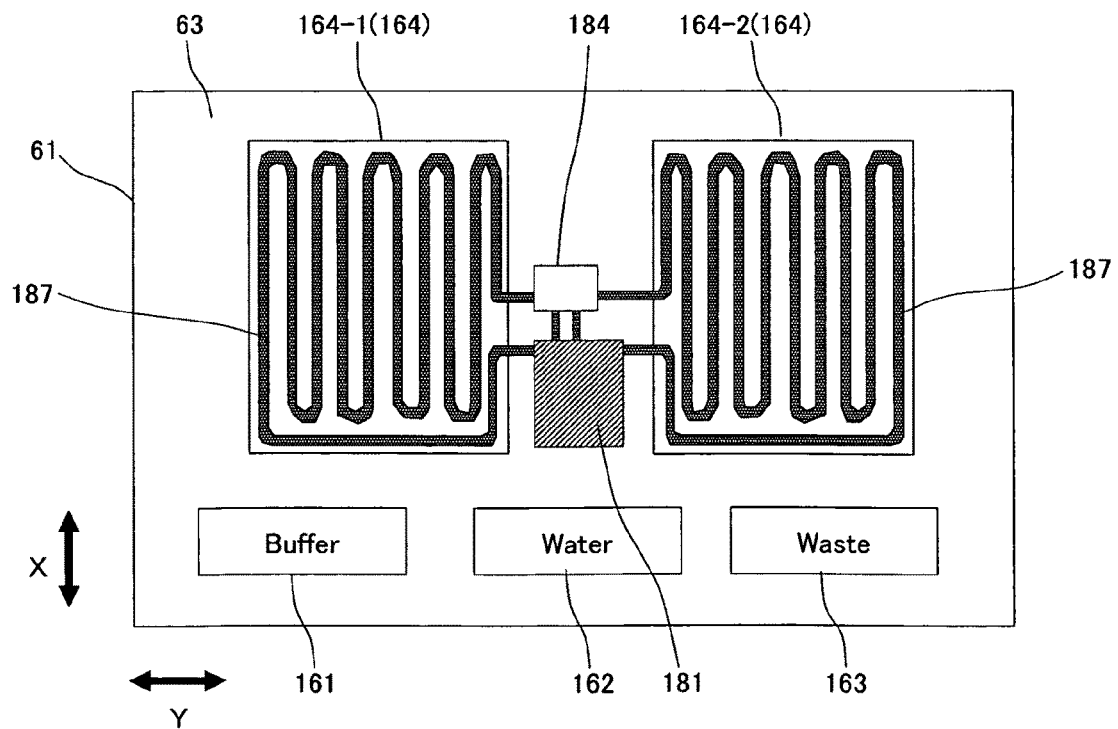

A cooling mechanism of a capillary electrophoresis apparatus according to a seventh embodiment is described with reference to FIG. 10A and FIG. 10B. FIG. 10A and FIG. 10B are block diagrams of the cooling mechanism of the capillary electrophoresis apparatus according to this embodiment.

FIG. 10A is a front schematic block diagram of the auto sampler unit 60 in this embodiment, and FIG. 10B is a plane block diagram of the table.

In this embodiment, a cold air generator 181 of the cooling mechanism is provided in a table area portion of the table 61 other than the areas where the buffer reservoir holder 161, the washing water reservoir holder 162, the waste reservoir holder 163, and the sample tray holders 164 (164-1, 164-2) are formed.

In this embodiment, the cold air generator 181 includes a Peltier element 182, a coolant tank 183, and a circulation pump 184.

In the illustrated example, a mounting hole 185 for the cold air generator 181 is formed in a table area portion between the two sample tray holders 164 (164-1, 164-2). In the mounting hole 185, the Peltier element 182 is provided with the endothermic surface (cooling surface) thereof facing the table top 63 side, i.e., the mounting side of the sample tray 70, and the exothermic surface (heat-radiating surface) thereof facing the rear surface side, that is, opposite to the table top 63. The coolant tank 183 for storing a coolant is provided abutting on the endothermic surface of the Peltier element 182. Moreover, in the mounting hole 185, a heat sink 186 is provided abutting on the exothermic surface of the Peltier element 182, so that a concavo-convex shaped heat-radiating portion thereof is exposed to the rear surface side of the table 61. The circulation pump 184 is arranged on the table top 63 in the vicinity of the mounting hole 185.

On the other hand, a circulation pipe 187 of the coolant is laid on the table top 63 of each of the sample tray holders 164

(164-1, 164-2) so that the coolant may be passed throughout the sample tray holders 164. One end of the circulation pipe 187 communicates with the discharge side of the circulation pump 184, while the other end of the circulation pipe 187 is connected to the intake side of the circulation pump 184 via the coolant tank 183.

Meanwhile, the sample tray 70 is formed so that the leg portions of the sample tray base 72 may surround the sample tray holder 164. In this embodiment, the inner peripheral surface of the leg portion of the sample tray 70 engages with a positioning portion 188 used for positioning, the positioning portion 188 being vertically installed from the table top 63 in a peripheral portion of the sample tray holder 164 of the table 61. The bottom of the sample tray base 72 is faced to the sample tray holder 164 on which the circulation pipe 187 is laid. Thus, the sample tray base 72 is held so as not to slide on the table top 63. Then, with the use of the leg portions and the bottom portion of the sample tray base 72 and the sample tray holder 164, the space 170 sealed with respect to the outside is formed in the sample tray 70.

In this embodiment, when the Peltier element 182 is driven by a non-illustrated driver circuit and the Peltier element 182 carries out cooling by means of this endothermic surface (cooling surface), the coolant of the coolant tank 183 is cooled. The cooled coolant of the coolant tank 183 circulates back to the coolant tank 183 after passing through the circulation pipe 187 by the circulation pump 184 which is similarly driven. At this time, the space 170 of the sample tray 70 is cooled by the coolant flowing through the circulation pipe 187, and the atmosphere (air) in the well receiving space 72b communicating with the space 170 is also cooled.

Accordingly, also in this embodiment, as in the case of the sixth embodiment, the effect is achieved, such as that the deterioration of the sample, held in the well 71, to be measured later can be suppressed. Note that, in this embodiment, the cold air generator 181 is installed in the table 61 of the auto sampler unit 60; however, the cold air generator 181 may be installed in a portion other than the auto sampler unit 60 of the capillary electrophoresis apparatus 1.

As described above, the embodiments of the capillary electrophoresis apparatus according to the present invention have been described; however, specific configurations of the cooling mechanism and the like are not limited to the above-described embodiments. For example, the configurations of the cooling mechanisms described in the second to fifth embodiments can be also employed to the configuration of a cooling mechanism arranged in the table 61 of the auto sampler unit 60, and the fan of the cooling mechanism described in the fifth embodiment can be incorporated into other embodiments.

Then, according to the capillary electrophoresis apparatuses and the sample trays of these embodiments described above, the deterioration of the sample, held in the well of the sample plate, to be measured later is suppressed. Moreover, the temperature condition of each sample held in each well is prevented from changing from the state of the measurement start to prevent a variation in the temperature conditions, at the time of the separation-analysis measurement, among samples held in the respective wells. As a result, even if the standby time until the measurement starts is extremely long, the occurrence of degeneration or deterioration of samples can be prevented and accurate measurement can be carried out with reliability.

Moreover, even if the standby time to the measurement becomes long at the time of electrophoresis (at the time of separation analysis) that is consecutively carried out a large number of times, a sample, in the sample plate, to be measured later can be cold-stored. Accordingly, the deterioration of the sample can be suppressed, and the sample can be used to the last electrophoresis measurement without being degraded, thus improving the reliability of the electrophoresis data with the capillary electrophoresis apparatus.

EXPLANATION OF REFERENCE NUMERALS 1 capillary electrophoresis apparatus
10 pump unit
11 flow path
12a to 12d flow path connector
12 polymer block
13 syringe
14 polymer bottle
15 buffer jar
16 electrode
17a polymer tube
17b buffer side tube
18 check valve
19 valve
20 oven unit
21 oven
30 capillary array
31 capillary
31a sample injection side
31b polymer injection side
32 conductive pipe
33 load header
34 detection window
35 capillary head
40 high voltage power supply unit
50 irradiation and detection unit
51 irradiation optical system
52 detection optical system
60 auto sampler unit
61 table
62 table transfer mechanism
63 table top
64 auto sampler base
70 sample tray
71 well
72 sample tray base
72a receiving opening
72b well receiving space
72c engagement groove
72d mounting hole
73 sample plate
74 septa
75 clip
90 buffer reservoir
92 washing water reservoir
94 waste reservoir
101 Peltier element
102 heat sink
103 metal plate
104 power cable
105 connector
106 sensor
107 communication cable
108 connector
109 driver circuit
110 power cable
111 thermal control circuit
112 communication cable
121 cooling block
122 well receiving hole 131 sealed container
132 coolant
141 fan
142 driver circuit
151 ice or coolant
161 buffer reservoir holder
162 washing water reservoir holder
163 waste reservoir holder
164 sample tray holder
165 mounting hole
166 Peltier element
167 metal plate
168 heat sink
169 positioning portion
170 space
171 communicating hole
181 cold air generator
182 Peltier element
183 coolant tank
184 circulation pump
185 mounting hole
186 heat sink
187 circulation pipe
188 positioning portion

What is claimed is:

1. A capillary electrophoresis apparatus comprising:
(a) an auto sampler configured to transport a sample tray to an injection side of a capillary in accordance with a predetermined procedure, the sample tray including a sample plate having a plurality of wells for holding samples, wherein the sample tray is mounted at a predetermined position on a table of the auto sampler;
(b) a cooling unit configured to cool the sample plate of the sample tray, wherein, the cooling unit is provided in the sample tray;
(c) a driving circuit configured to drive the cooling unit;
(d) a sensor configured to detect a temperature of a space in the sample tray that accommodates the sample plate having the plurality of wells;
(e) a thermal control circuit configured to control a drive of the driving circuit in accordance with the temperature detected by the sensor;
(f) a signal line connecting the sensor and the thermal control circuit; and
(g) a power cable connecting the driving circuit and the cooling unit.

2. A capillary electrophoresis apparatus comprising:
(a) an auto sampler configured to transport a sample tray to an injection side of a capillary in accordance with a predetermined procedure, the sample tray including a sample plate having a plurality of wells for holding samples;
(b) a cooling unit configured to cool the sample plate of the sample tray;
(c) a driving circuit configured to drive the cooling unit;
(d) a sensor configured to detect a temperature of a space in the sample tray that accommodates the sample plate having the plurality of wells;
(f) a thermal control circuit configured to control a drive of the driving circuit in accordance with the temperature detected by the sensor;
(g) a signal line connecting the sensor and the thermal control circuit; and
(h) a power cable connecting the driving circuit and the cooling unit, wherein:
the sample tray is mounted at a predetermined position on a table of the auto sampler,
the table is configured to be movable to transport the sample tray,
the sample tray includes a first connector,
the table includes a second connector configured to be connected to the first connector;
the sensor and the thermal control circuit are connected by the signal line via the first and second connectors that are connected together, and
the driving circuit and the cooling unit are connected by the power cable via the first and second connectors that are connected together.

3. A sample tray comprising:
a sample plate in which a plurality of sample holes for holding samples are formed in an array;
a sample tray base which holds the sample plate;
a septum which prevents the samples held in the sample holes from evaporating; and
a clip which engages with the sample tray base holding the sample plate and integrally holds the sample late and the septum to the sample tray base, to thereby hold the sedum toward an opening side of the sample holes of the sample plate,
wherein the sample tray base includes:
a cooling unit positioned so as to face the sample plate,
a sensor configured to detect a temperature of a space on the sample tray base that holds the sample plate in which the plurality of sample holes are formed in an array,
a signal line for connecting the sensor and a thermal control circuit configured to control a drive of the driving circuit in accordance with the temperature detected by the sensor, and
a power cable for connecting a driving circuit configured to drive the cooling unit, wherein:
the sample tray base is mounted at a predetermined position on a table of an auto sampler and is movable;
the sample tray base includes a first connector,
the table includes a second connector configured to be connected to the first connector,
the sensor and the thermal control circuit are connected by the signal line via the first and second connectors that are connected together, and
the driving circuit and the cooling unit are connected by the power cable via the first and second connectors that are connected together.

* * * * *